United States Patent [19]

Cutayar et al.

[11] Patent Number: 4,978,545

[45] Date of Patent: Dec. 18, 1990

[54] PROCESS FOR THE CONTROLLED OXYGENATION OF AN ALCOHOLIC FERMENTATION MUST OR WORT

[75] Inventors: Jacques-Marcel Cutayar, Guyancourt; Dominique Poillon, Igny; Sylvie Cutayar, Guyancourt, all of France

[73] Assignee: L'Air Liquide, Societe Anonyme pour l'Etude et L'Exploitation des Procedes Georges Claude, Paris, France

[21] Appl. No.: 326,062

[22] Filed: Mar. 21, 1989

[30] Foreign Application Priority Data

Mar. 22, 1988 [FR] France .................. 88 03705

[51] Int. Cl.$^5$ .................. C12G 1/00; A23B 7/144
[52] U.S. Cl. .................. 426/312; 426/11; 426/16; 426/474
[58] Field of Search .............. 426/11, 15, 16, 30, 426/231, 312, 474, 477

[56] References Cited

U.S. PATENT DOCUMENTS 4,652,451  3/1987  Leedham et al. .................. 426/16

FOREIGN PATENT DOCUMENTS 0103988  3/1984  European Pat. Off. .
0160442  11/1985  European Pat. Off. .
1518261  7/1978  United Kingdom .
2197341  5/1988  United Kingdom .

OTHER PUBLICATIONS

"A method for supplying oxygen to a fermentation liquor during mainly unaerobic fermentation in a fermentor for achieving growth of a microorganism contained in the fermentation liquor", *Research Disclosure*, No. 272, Dec. 1986, No. 27254, p. 738.

"An integrated Bioreactor–Separator: In Situ Recovery of Fermentation Products by a Novel Membrane-Based Dispersion-Free Solvent Extraction Technique", *Biotechnology and Bioengineering Symp.*, No. 17, 1986, By G. Frank et al., pp. 303–316.

*Primary Examiner*—Donald E. Czaja
*Assistant Examiner*—Helen Pratt
*Attorney, Agent, or Firm*—Young & Thompson

[57] ABSTRACT

The process comprises putting the must or wort in contact with a side of a membrane permeable to oxygen and putting the other side of this membrane in contact with a gas containing oxygen under partial pressure higher than the partial pressure in oxygen of the liquid. Application in vinification.

5 Claims, 1 Drawing Sheet

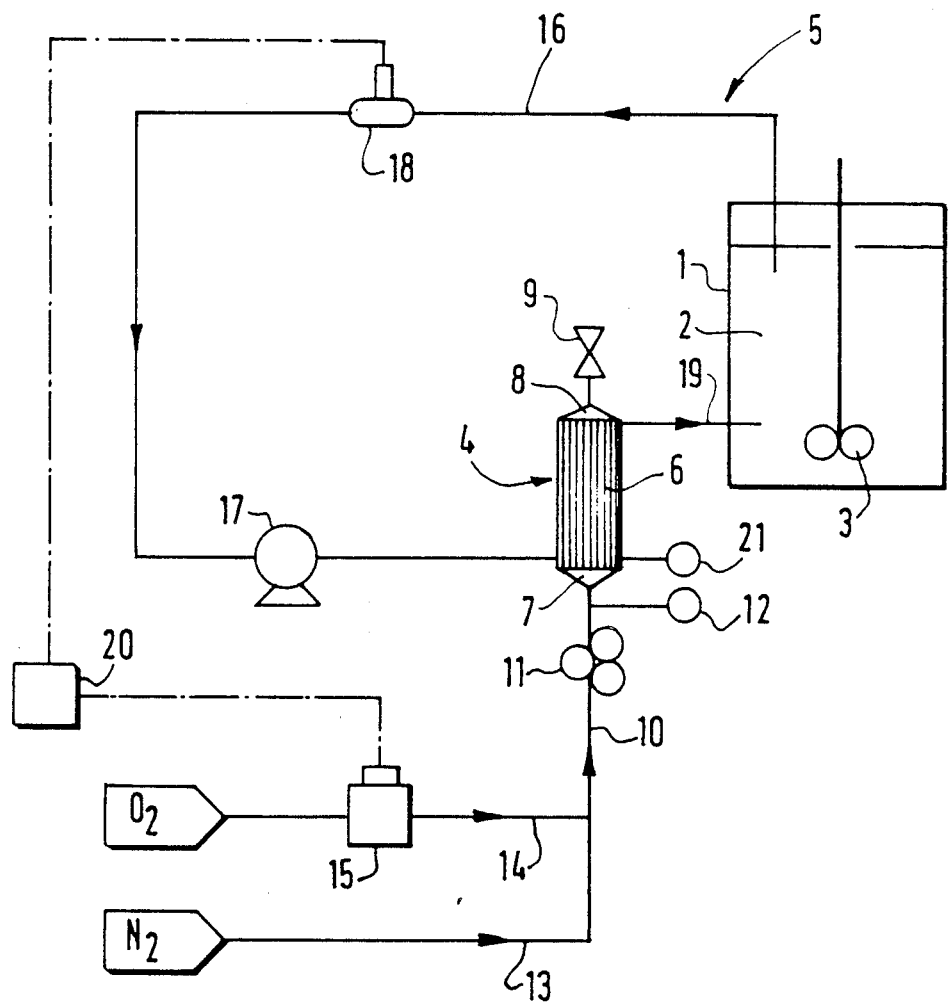

PROCESS FOR THE CONTROLLED OXYGENATION OF AN ALCOHOLIC FERMENTATION MUST OR WORT

The present invention relates to alcoholic fermentation. It is in particular applicable to the techniques of vinification, brewery, cider-making, distillery, etc.

As is well known, alcoholic fermentation is the biological reaction in the course of which the sugars having 6 carbon atoms (hexoses) are converted into ethanol by yeasts.

A feature of alcoholic fermentation is that the ethanol produced is an inhibitor of the reaction (retro-inhibition). This results in an increasingly large reduction in the rate of production of the ethanol when the latter accumulates in the fermentation must or wort, this phenomenon continuing until the complete stoppage of the reaction.

It is important in alcoholic fermentation to employ yeasts having a good resistance to the ethanol (alcoholresistance), so as to reduce the fermentation time (improved activity) and/or increase the degree of alcohol of the must or wort at the end of fermentation.

It has been shown that the resistance to alcohol is proportional to the concentration of unsaturated lipids and sterols in the yeasts. These compounds are the essential constituents of their cellular membrane and are only synthesized and accumulated in the presence of oxygen.

When the alcoholic fermentation has started, the oxygen initially present in the must or wort is rapidly consumed and the yeasts then continue to ferment and develop in anaerobiosis. There is then a utilization and redistribution of the unsaturated lipids and sterols (which are no longer biosynthesized) which serve to produce the membranes of the daughter cells. Consequently, there is a continuous drop in their concentration in the yeasts resulting in an increasingly high sensitivity to ethanol up to a complete inhibition of the fermentation (it is estimated that this inhibition becomes effective at the end of four to five generations).

To avoid or delay this phenomenon, the fermentation must or wort must be oxygenated before the initially present dissolved oxygen is completely consumed. This operation is generally carried out by what is termed in the industry a "raising of the musts or worts" consisting in pumping the must or wort at the base of the vat so as to discharge it at the top; the aeration then occurs from the gaseous atmosphere at the top and permits reaching a concentration of dissolved oxygen on the order of 4 to 5 mg/liter. This operation is usually carried out daily and during a short period (a few tens of minutes).

However, it has been shown that an excessively large concentration of dissolved oxygen might alter the organoleptic qualities of the wine:

alteration of the taste: risks of oxidation of certain compounds (ethanol into acetaldehyde or even into acetic acid . . . );

alteration of the colour: essentially with regard to white wines, risks of enzymatic browning (action of the polyphenoloxidases . . . ).

It can be assumed that in practice, these phenomena appear when the concentration of dissolved oxygen exceeds 0.1 to 0.5 mg/l depending on the treated must or wort.

Under these conditions, it could occur that the must or wort raising technique is not the best adapted since it affords no control of the oxygen transfer and therefore does not permit avoiding the aforementioned problems.

For the purpose of achieving an improved control of the oxygenation of the must or wort, it has been proposed to effect a bubbling of an atmosphere poor in oxygen (dilution of air with nitrogen) so as to avoid any local superoxygenation in the region of the gas/liquid interface. However, bearing in mind on one hand the low concentration of oxygen in the aeration gas (0.5 to 2%) and on the other hand the requirement in oxygen of the yeasts, such a system results in the use of appreciable aeration flows which inevitably result in losses of ethanol.

An object of the invention is to provide a technique for obtaining a well-controlled oxygenation of the must or wort with no consecutive loss of ethanol.

The invention therefore provides a process for the controlled oxygenation of an alcoholic fermentation must or wort, which comprises putting the must or wort in contact with one side of a membrane permeable to oxygen; putting the other side of said membrane in contact with a gas containing oxygen under a partial pressure higher than the partial pressure in oxygen of the liquid; maintaining the ratio of the pressure of the gas to the pressure of the must or wort constant; and regulating the oxygenation of the must or wort by varying the oxygen content of the gas.

Preferably, there is employed as the gas a mixture of oxygen and a neutral gas, in particular an oxygen/nitrogen mixture.

The invention also provides a plant for carrying out such a process. This alcoholic fermentation plant is of the type comprising a fermentor containing a fermentation must or wort, and means for the oxygenation of said must or wort, the oxygenation means comprising a permeator including a membrane permeable to the oxygen; means for putting one side of the membrane in contact with the must or wort; and means for bringing a gas containing oxygen in contact with the other side of said membrane, said means bringing the gas comprising a source of a neutral gas, in particular nitrogen, a source of oxygen, means for metering and mixing the neutral gas and the oxygen, and a pressure reducer located on the downstream side of the metering and mixing means.

An example of carrying out the invention will now be described with reference to the accompanying drawing in which the single FIGURE is a diagrammatic view of an alcoholic fermentation plant according to the invention.

The plant shown in the drawing mainly comprises a fermentation vat or fermentor 1 containing a fermentation must or wort 2 and provided with a stirrer 3, a permeator 4 and a circuit 5 for circulating the must or wort between the fermentor 1 and the permeator 4.

The permeator 4 is formed by at least one membrane module of the type having hollow fibres These fibres extend in a housing 6 between a gas inlet header 7 and a gas outlet header 8. Each fibre is constituted by a microporous membrane permeable to oxygen, for example formed from polypropylene or a thin layer of silicone applied to a macroporous support layer Such permeation modules are commercially available and there may be employed for example a module "ENKA model LM2P12" which comprises 22 hollow fibres of polypropylene having an outside diameter of 1.8 mm and an inside diameter of 1.2 mm, the total exchange surface being 0.03 sq. m.

The outlet header 8 comprises a valve 9 for communication with the open air, while the inlet header 7 is connected to a gas supply conduit 10 provided with a pressure reducer 11 and, on the downstream side of the latter, with a pressure gauge 12. The conduit 10 is itself supplied by a nitrogen conduit 13 and by an oxygen conduit 14 provided with a unit mass flowmeter 15.

The circuit 5 comprises a conduit 16 extending from the fermentor to the permeator and equipped with a pump 17 and an ammeter probe 18 for measuring the concentration of the dissolved oxygen in the must or wort. This probe may be for example the probe known by the trade name "ORBISPHERE". The conduit, 16 leads to one end of the housing of the permeator 4, and another conduit 19 extends from the other end of this housing to the fermentor.

The flowmeter 15 is controlled by the signals delivered by the probe 18 through a regulator 20 of the PID type, and a pressure gauge 21 measures the pressure $P_L$ of the liquid in the housing of the permeator which is a function of the flow of the pump 17 for a given must or wort.

In operation, the must or wort flows in the circuit 5 and an oxygen/nitrogen mixture is sent into the header 7 of the permeator and thence into the hollow fibres at a pressure $P_G$. The ratio $P_G/P_L$ is maintained constant slightly below the critical value resulting in bubbles occurring in the liquid. The transfer of oxygen can then be controlled by varying solely the composition of the gas introduced in the permeator.

For this purpose, there is chosen as a set point of the probe 18 a variable of about 0.1 to 0.5 mg $0_2/l$, which is the value beyond which a superoxygenation unfavourable to the must or wort may be considered to exist. The probe 18 thus regulates the flowmeter 15 for controlling the flow of oxygen which comes to be mixed with the flow of nitrogen supplied through the conduit 13, assumed to be constant. The mixture is then expanded at 11 for delivering to the permeator at a constant pressure in agreement with the optimum ratio $P_G/P_L$.

Thus, oxygen is permanently transferred in a controlled manner into the must or wort and this solely in the dissolved form, which avoids losses of ethanol by evaporation.

The use of the circuit 5 outside the fermentor affords advantages of convenience, for example as concerns maintenance, but requires a sufficient fluidity of the must or wort. In some cases (for example fermentation of red wines) it will be preferable to dispose the permeation fibres directly in the fermentor 1 or to employ a filtration device at the entrance of the circuit 5.

Comparative tests have been carried out in the case of a white wine, on one hand with a plant according to the invention and on the other hand with a reference fermentor oxygenated by the convential must raising technique. These tests showed an improved tolerance with respect to ethanol of the yeasts in the fermentor oxygenated in accordance with the invention, and a distinctly increased specific consumption of glucose, at least for concentrations of ethanol of 10% Vol and 11% Vol:

| Concentration of ethanol | Specific consumption of glucose grams glucose/grams yeast · hour | |
|---|---|---|
| | Reference fermentor | Controlled oxygenation fermentor |
| 9% Vol | 0.34 | 0.35 |
| 10% Vol | 0.22 | 0.26 |
| 11% Vol | 0.09 | 0.13 |

It is clear from these tests that the invention permits increasing the fermenting activity, i.e., the rates of fermentation. Furthermore, chromatographic analyses have revealed the absence of oxidized compounds (acetaldehyde, acetic acid . . . ) which could have appeared in the case of the superoxygenation of the must or wort.

We claim:

1. A process for controlled oxygenation of alcoholic fermentation must or wort with a gas containing oxygen, comprising the steps of simultaneously applying the must or wort at a first pressure on one side of an oxygen-permeable membrane and applying the oxygen-containing gas at a second pressure on an opposite side of the membrane, controlling a supply of the oxygen-containing gas such that the partial pressure of oxygen in the gas is higher than the partial pressure of oxygen in the must or wort, maintaining a substantially constant ratio of the second pressure to the first pressure, and selectively regulating the oxygen content of the gas to achieve a desired degree of oxygenation of the must or wort.

2. The process according to claim 1, wherein the pressure of the gas in contact with the membrane is maintained below a value at which bubbles would occur within the must or wort.

3. The process according to claim 1, further comprising measuring the concentration of dissolved oxygen in the must or wort, and varying the oxygen content of the gas in such a manner as to maintain the concentration at about a constant value.

4. The process according to claim 1, wherein the gas is a mixture of oxygen and a neutral gas.

5. The process according to claim 1, wherein the gas is a mixture of oxygen and nitrogen.

* * * * *